United States Patent [19]

Van Scott et al.

[11] 4,234,599

[45] * Nov. 18, 1980

[54] TREATMENT OF SKIN KERATOSES WITH α-HYDROXY ACIDS AND RELATED COMPOUNDS

[76] Inventors: Eugene J. Van Scott, 1138 Sewell La., Rydal, Pa. 19046; Ruey J. Yu, 4 Lindenwold Ave., Ambler, Pa. 19002

[*] Notice: The portion of the term of this patent subsequent to Oct. 26, 1993, has been disclaimed.

[21] Appl. No.: 948,489

[22] Filed: Oct. 4, 1978

[51] Int. Cl.$^3$ .................... A61K 31/335; A61K 31/16
[52] U.S. Cl. .................................. 424/279; 424/283; 424/285; 424/311; 424/316; 424/317; 424/318; 424/320; 424/325; 424/329
[58] Field of Search ............... 424/316, 317, 279, 283, 424/320, 311, 318, 329

[56] References Cited

U.S. PATENT DOCUMENTS

| | | | |
|---|---|---|---|
| 3,666,863 | 5/1972 | Swanbeck | 424/316 |
| 3,988,470 | 10/1976 | Van Scott et al. | 424/283 |
| 4,105,783 | 8/1978 | Yu et al. | 424/283 |

OTHER PUBLICATIONS

Handbook of New Prescription Drugs–5th ed., 1977.

*Primary Examiner*—Leonard Schenkman
*Attorney, Agent, or Firm*—Leblanc, Nolan, Shur & Nies

[57] ABSTRACT

Preventive as well as therapeutic treatment to alleviate the symptoms of skin keratoses consisting of topical application of a solution, gel, lotion, cream or ointment containing one or more of the α- or β-hydroxy acids or α-keto acids, esters thereof, and their amine salts is disclosed. The compounds include free acid or amine salt forms of α-hydroxy-butyric acid, α-hydroxyisobutyric acid, α-hydroxyisocaproic acid, α-hydroxyisovaleric, atrolactic acid, β-hydroxybutyric acid, β-phenyl lactic acid, β-phenylpyruvic acid, citric acid, ethyl pyruvate, galacturonic acid, glucoheptonic acid, glucoheptono 1,4-lactone, gluconic acid, gluconolactone, glucuronic acid, glucuronolactone, glycolic acid, isopropyl pyruvate, lactic acid, malic acid, mandelic acid, methyl pyruvate, mucic acid, pyruvic acid, saccharic acid, saccharic acid 1,4-lactone, tartaric acid, and tartronic acid. The therapeutic composition may include one or more of the compounds present in the total amount of from three to thirty percent. Topical application to affected areas has been found to achieve from substantial to complete remissions of the keratoses in humans.

25 Claims, No Drawings

TREATMENT OF SKIN KERATOSES WITH α-HYDROXY ACIDS AND RELATED COMPOUNDS

This is related to our copending patent applications Ser. Nos. 720,787 and 720,835, both filed Sept. 7, 1976 now U.S. Pat. Nos. 4,105,782 and 4,105,783 respectively. Said parent applications are related to our patent application Ser. No. 598,224, filed July 23, 1975, now U.S. Pat. No. 4,021,572, which in turn is a continuation-in-part of our patent applications Ser. No. 556,423 and Ser. No. 556,424, filed Mar. 7, 1975, now U.S. Pat. Nos. 3,988,470 and 3,984,566, respectively, which are divisions of our patent application Ser. No. 445,231, filed Feb. 25, 1974, now U.S. Pat. No. 3,920,835, which in turn was a continuation-in-part of our patent application Ser. No. 394,269, filed Sept. 4, 1973, now U.S. Pat. No. 3,879,537. The disclosures of our above identified patents and patent applications are hereby incorporated by reference.

Keratoses of the skin may be classified into two groups, namely actinic and non-actinic keratoses. Actinic keratoses, also known as solar or senile keratoses, are found most commonly in Caucasians with fair colored skin, and almost exclusively in persons with poor ability to tan. Development of actinic keratoses is quite common among these people who live in sunny climates such as Australia or the southern United States.

Lesions of actinic keratoses are found only in the sunlight exposed areas of the body such as on the face, hands and forearms. The clinical lesion usually consists of a scaly plaque less than 1 cm in diameter with freckled pigmentation varying from yellow, brown to blackish depending on the amount of adherent horny material. In addition, there is usually a pinkish tinge of the entire lesion or a red periphery. Without any treatment actinic keratoses may take one of three courses: (a) disappear spontaneously, (b) stay the same, (c) evolve into epidermal carcinoma.

The nonactinic keratoses may be associated with aging and variously include lesions known as seborrheic warts, liver spots, acrokeratoses and other names. Clinical features of nonactinic keratoses are often similar to those of actinic keratoses but are usually distinguishable by size, absence of erythema, differing degrees of pigmentation and not being confined to sunlight-exposed areas of the skin.

Common treatments for actinic and nonactinic keratoses (hereinafter referred to collectively as keratoses) include surgical removal of the lesions, electrodessication, freezing with dry ice or liquid nitrogen, or topical administration of 5-fluorouracil. Surgical management is not necessarily desirable due to clinical conditions such as number and size of the lesions, and the resulting cosmetic disfigurements. Topical treatment then is in many cases the desirable approach.

The use of 1% to 5% 5-fluorouracil for topical treatment of actinic keratoses is effective in eradicating the lesions. However, the use of 5-fluorouracil has the following shortcomings. When this compound is used for topical treatment of the keratoses erythema develops after 3 or 4 days of twice-daily application, and an inflammatory response follows that is roughly proportional to the amount of skin damage. Discomfort and local tenderness are common, and pain and ulceration frequently occur. The peak response occurs about two week after treatment is started, and there may be unsightly and extensive soft tissue swelling.

Topical treatment of the keratoses with 5-fluorouracil has been considered to be safe and devoid of internal toxic side effects. However it is well documented that 5-fluorouracil when given systemically to humans induces delayed type clinical toxicity. The earliest toxic symptoms are anorexia and nausea; these are followed shortly after with stomatitis and diarrhea. Stomatitis may be preceded by a sensation of dryness, followed by erythema and formation of a white, patchy membrane that develops into ulceration and necrosis. The major toxic effects, however, result from the myelosuppressive action of this drug, manifested as leukopenia, thrombocytopenia and anemia. Loss of hair, occasionally progressing to total alopecia, nail changes, dermatitis, and atrophy of the skin may be encountered. Neurological toxic symptoms have been reported, and myelopathy has been found after systemic administration of this drug.

It is therefore desirable to develop other efficacious drugs, preferably of physiologic origin, which do not caus irritation, pain, allergic reaction or systemic toxicity during or after the topical treatment of keratoses.

In our U.S. Pat. No. 4,034,114, issued July 5, 1977, and entitled TREATMENT OF SKIN KERATOSES WITH RETINAL, a treatment was described for skin keratoses with vitamin A aldehyde. As described in our aforementioned patent, topical application of the therapeutic composition containing from 0.01 to 2 percent of vitamin A aldehyde was found to be effective against both actinic and nonactinic keratoses in humans.

In our previous application Ser. No. 445,231, filed Feb. 25, 1974, now U.S. Pat. No. 3,920,835, and entitled TREATMENT OF DISTURBED KERATINIZATION, a treatment was described for dandruff, acne and palmer and plantar hyperkeratosis.

As described in our aforementioned application, certain lower aliphatic compounds having two to about six carbon atoms and preferably having α-carbon functionality were found to be effective agents against dandruff, acne and palmar and plantar hyperkeratosis. These compounds include glycolic acid, citric acid, malic acid, tartronic acid, methyl pyruvate, ethyl pyruvate, α-hydroxyisobutyric acid and α-hydroxybutyric acid.

In our prior application Ser. No. 598,224, now U.S. Pat. No. 4,021,572, it was disclosed that certain salts of lactic acid or lactic anhydride, lactamides and quarternary ammonium lactates were effective upon topical application to treat the lesions of acne vulgaris. Furthermore, it was disclosed in our patent applications Ser. Nos. 720,787 and 720,835, filed Sept. 7, 1976, that certain salts of several lower aliphatic α-hydroxy acids and closely related compounds were also effective in the treatment of acne vulgaris and in the treatment of dandruff and dry skin.

We have now discovered that actinic and nonactinic keratoses also may be successfully prevented or treated with the free acid form or certain salts of α-hydroxy acids and closely related compounds. These compounds include α-hydroxy-butyric acid, α-hydroxyisobutyric acid, α-hydroxyisocaproic acid, α-hydroxyisovaleric acid, atrolactic acid, β-hydroxybutyric acid, β-phenyl lactic acid, β-phenylpyruvic acid, citric acid, ethyl pyruvate, galacturonic acid, glucoheptonic acid, glucoheptono 1,4-lactone, gluconic acid, gluconolactone, glucuronic acid, glucuronolactone, glycolic acid, isopropyl pyruvate, lactic acid, malic acid, mandelic acid, methyl pyruvate, mucic acid, pyruvic acid, saccharic acid, saccharic acid 1,4-lactone, tartaric acid, and tartronic acid.

It has been established through tests on humans having keratoses that topical application of a solution, gel, lotion, cream or ointment containing from 3-to-30 percent of at least one acid, amide or the ammonium salt of the present invention, and preferably from 5 to 20 percent thereof, is therapeutically effective, when applied usually on a once or twice daily basis, but less frequently in some instances, to eradicate, within about three to eight weeks time, keratotic lesions and to restore the affected areas to a normal skin appearance or at least to a state of substantial improvement thereof.

Accordingly, it is the object of this invention to provide a relatively nontoxic, nonallergenic medicinal composition which when topically applied will reliably eradicate or improve the symptoms and signs of keratoses.

It is another object to provide a method for treating keratoses with a nonirritating and nontoxic cream, ointment, gel or solution containing at least one of the α-hydroxy acids or closely related compounds.

It is still another object to provide a safe and efficient method for treating the symptoms of keratoses through regular topical application of a medicinal composition containing α-hydroxy acids or closely related compounds, their amides or ammonium salts, which will promote healing within about three to eight weeks.

Specifically, the compounds of this invention found to be useful in the treatment of keratoses are α-hydroxy acids, β-hydroxy acids, α-keto acids, or certain salt forms, present in a vehicle in a concentration of from 3-to-30 percent, by weight.

The salt form of the compounds of this invention is a reaction product of the acid with ammonia or any organic primary, secondary, tertiary or quaternary amine. The reaction products of this invention are ammonium salts or amine salts of the above identified compounds. In the interest of uniformity and to avoid confusion, the reaction products of this invention as above defined will be referred to herein generally as amine salt.

Preferred organic primary amines may include any alkylamines such as methylamine and ethylamine; ethanolamines such as monoethanolamine and monoisopropanolamine; and diamines such as ethylenediamine and 1,2-diaminopropane.

Preferred organic secondary amines may include dialkylamines such as dimethylamine and diethylamine; diehanolamine and di-isopropanolamine; N-methylethanolamine and N-ethylethanolamine.

Preferred organic tertiary amines may include trialkylamines such as trimethylamine and triethylamine; triethanolamine; N-methyldiethanolamine and tri-isopropanolamine. The quaternary ammonium hydroxide includes basic choline.

PREPARATION OF THE THERAPEUTIC COMPOSITIONS

In order to prepare the compositions of this invention, at least one of the α-hydroxy acids, β-hydroxy acids, α-keto acids, or their amine salts is preferably dissolved in water and/or ethanol initially. The solution thus prepared may be admixed in the conventional manner with commonly available lotion, creme or ointment bases such as hydrophilic ointment (USP) or petrolatum. The concentration of the compound ranges from 3-to-30 percent by weight of the total composition. The preferred concentration range, however, is from 5-to-20 percent.

If desired, two or more of the above compounds may be admixed in a lotion, creme or ointment as described above to form a composition of this invention. In this instance, it is preferred that the concentration of the compounds not exceed a total of 15 percent by weight.

The water or ethanol used to dissolve the compound according to this invention may range in concentration of from 1-to-30 percent by volume of the total composition. The preferred concentration thereof, however, is 10 percent by volume.

It has been found that the therapeutic creams or ointments of this invention, prepared as above, may be stored in cream or ointment jars at room temperature for extended periods of time without a change in clinical effectiveness.

The above compounds may also be prepared in a solution or gel form. A typical solution of this invention utilizes at least one of the above compounds, dissolved directly in a mixture of water, ethanol and propylene glycol in a volume ratio of 40:40:20 respectively. The ratio of each vehicle may vary, however the preferred concentrations of ethanol and propylene glycol should not exceed 70 percent and 30 percent respectively. When solutions are formulated according to this invention, the compound concentration range may be from 3-to-30 percent by weight as above. In addition, a concentration of from 5-to-20 percent is preferred. One or more of the compounds may also be admixed to a total concentration not exceeding about 15 percent by weight, as described above.

A typical gel preparation of this invention utilizes at least one of the above compounds, dissolved directly in a mixture of water, ethanol and propylene glycol in a volume ratio of 30:60:10 respectively. A gelling agent such as hydroxyethylcellulose, hydroxypropylcellulose or hydroxypropyl methylcellulose is then added to the mixture with agitation. The concentration of the gelling agent may range from 0.1-to-5 percent by weight of the total composition. The preferred concentration, however, is from 1-to-3 percent.

From a practical point of view, an amine salt of the α-hydroxy acid, β-hydroxy acid or α-keto acid is more conveniently prepared in situ during the formulation of a composition. In this instance, one of the α-hydroxy acids, β-hydroxy acids or α-keto acids is dissolved in water and/or ethanol. Ammonium hydroxide or a certain organic base is then added to the above solution. Generally, a composition of this formulation should have a pH of the solution, gel, lotion, cream or ointment between 3.0 and 7.5.

Preferred organic bases include organic, primary, secondary, tertiary and quaternary amines. The organic primary amine may include alkylamines such as methylamine and ethylamine; ethanolamine such as monoethanolamine and monoisopropanolamines; diamines such as ethylenediamine and 1,2-diaminopropane. The organic secondary amines include dialkylamines such as dimethylamine and diethylamine, diethanolamine and diisopropanolamine; N-methylethanolamine and N-ethylethanolamine. The organic tertiary amines include trialkylamines such as triethylamine and triethylamine; triethanolamine; N-methyldiethanolamine and tri-isopropanolamine. The quaternary compounds preferably include basic choline.

The following are illustrative examples of formulations of compositions according to this invention. Although the examples utilize only selected formulations useful according to this invention, it should be understood that the following examples are illustrative and not limited. Therefore, any of the aforementioned acids and amines may be substituted according to the teachings of this invention in the following formulations.

EXAMPLE 1

Mandelic acid 10 percent cream or ointment is prepared as follows.

DL-Mandelic acid 10 gm is dissolved in 10 ml of ethanol, and the solution admixed with 80 gm of hydrophilic ointment, U.S.P. Continue agitation until a uniform consistency is obtained.

EXAMPLE 2

Mandelamide 5 percent cream or lotion is prepared as follows. First the mandelamide is synthesized from ethylmandelate (110 gm) and concentrated ammonium hydroxide (250 ml) by mixing them at room temperature. White crystalline mandelamide (80 gm) thus synthesized is washed thoroughly with water and dried. The product has a mobility (Rf) of 0.67 on thin layer chromatogram (silica gel) in a solvent system of methanol: benzene, 1:1.

Part A:

Polyoxyethylene (40) stearate: 2 gm
Polyoxyethylene (20) sorbitan monooleate: 1 gm
Glycerol monostearate: 4 gm
Beeswax: 2 gm
Cetyl alcohol: 3 gm
Isopropyl myristate: 1 gm Part B:

Water: 76 ml
Propylene glycol: 5 ml
Carbomer 934: 0.5 gm

Heat Part A to 75° C. and heat Part B to 80° C. Add Part B slowly to Part A with agitation. DL-Mandelamide 5 gm as synthesized above is added to the mixture. Continue agitation until the mixture is congealed.

EXAMPLE 3

Mandelic acid 20 percent gel is prepared as follows. DL-Mandelic acid 20 gm is dissolved in 50 ml of ethanol and the solution admixed with 23 ml of water and 5 ml of propylene glycol. Hydroxypropylcellulose, 2 gm is added to the mixture with agitation. Continue agitation until a uniform gel is formed.

EXAMPLE 4

Gluconolactone 10 percent solution is prepared as follows. D-Gluconolactone 10 gm is dissolved in 63 ml of water and the solution admixed with 18 ml of ethanol and 9 ml of propylene glycol.

EXAMPLE 5

Ethanolammonium mandelate 10 percent cream is prepared as follows.

Part A:

Polyoxyethylene (40) stearate: 2 gm
Polyoxyethylene (20) sorbitan monooleate: 1 gm
glycerol monostearate: 4 gm
Cetyl alcohol: 4 gm
Beeswax: 3 gm
Isopropyl myristate: 1 gm Part B:

Water 66 ml
Propylene glycol: 5 ml
Carbomer 940: 0.5 gm

Heat Part A to 75° C. and heat Part B to 80° C. Add Part B slowly to Part A with agitation. DL-Mandelic acid 10 gm and ethanolamine 3 ml are added to the mixture. Continue agitation until the mixture is congealed.

EXAMPLE 6

Gluconolactone 5 percent cream is prepared as follows. Gluconolactone 5 gm is dissolved in 10 ml of water, and the solution admixed with 85 gm of hydrophilic ointment, USP. Continue agitation until a uniform consistency is obtained.

EXAMPLE 7

Gluconic acid triethanolamine salt 5 percent cream is prepared as follows.

Part A:

Polyoxyethylene (40) stearate: 2 gm
Polyoxyethylene (20) sorbitan monooleate: 1 gm
Glycerol monostearate: 4 gm
Beeswax: 5 gm
Cetyl alcohol: 4 gm
Mineral oil: 2 gm Part B:

Water: 60 ml
Propylene glycol: 5 ml
Sorbitol: 3 gm
Glycerol: 3 ml
Carbomer 940*: 0.2 gm.

*Carbomer, also known as Carbopol is carboxy vinyl polymer resin manufactured by B. F. Goodrich Chemical Company, Cleveland, Ohio. Carbomer 940 has a molecular weight of about 4,000,000.

Heat Part A to 75° C. and heat Part B to 80° C. Add Part B slowly to Part A with agitation. Gluconolactone 5 gm and triethanolamine 2.5 gm are added to the mixture. Continue agitation until the mixture is congealed. Squalene 1 gm, tocopherylacetate 1 gm and retinol palmitate 1 gm are added to the cream with agitation.

EXAMPLE 8

Gluconic acid triethanolamine salt 5 percent lotion is prepared as follows.

part A:

Polyoxyethylene (40) stearate: 2 gm
Polyoxethylene (20) sorbitan monooleate: 1 gm
Glycerol monostearate: 4 gm
Beeswax: 3 gm
Cetyl alcohol: 3 gm
Mineral oil: 2 gm
Chicken fat: 2 gm Part B:

Water: 61 ml
Propylene glycol: 5 ml
Sorbitol: 3 gm
Glycerol: 3 ml
Carbomer 940: 0.2 gm Heat Part A to 75° C. and heat Part B to 80° C. Add Part B slowly to Part A with agitation. Gluconolactone 5 gm and triethanolamine 2.5 gm are added to the mixture. Continue agitation until the mixture is congealed. Squalene 1 gm, tocopherylacetate 1 gm and retinol palmitate 1 gm are added to the lotion with agitation.

EXAMPLE 9

Tartaric acid triethanolamine salt 5 percent cream is prepared as follows.

Part A:

Polyoxyethylene (40) stearate: 2 gm
Polyoyethylene (20) sorbitan monooleate: 1 gm
Glycerol monostearate: 4 gm
Beeswax: 5 gm
Cetyl alchol: 4 gm
Mineral oil: 2 gm Part B:

Water: 56 ml
Propylene glycol: 5 ml
Sorbitol: 3 gm
Glycerol: 3 ml
Carbomer 940: 0.2 gm Heat Part A to 75° C. and heat Part B to 80° C. Add Part B slowly to Part A with agitation. Tartaric acid 5 gm and triethanolamine 6 gm are added to the mixture. Continue agitation until the mixture is congealed. Squalene 1 gm, tocopherylacetate 1 gm and retinol palmitate 1 gm are added to the cream with agitation.

EXAMPLE 10

Mandelic acid 20% nonaqueous solution is prepared as follows. DL-Mandelic acid 20 gm is dissolved in 64 ml of ethanol, and the solution admixed with 16 ml of isopropyl myristate. The solution thus prepared may be stored in brown dropper bottles.

EXAMPLE 11

Glycolic acid 10 percent solution is prepared as follows.

Glycolic acid 10 gm is dissolved in 20 ml of water, and the solution admixed with 50 ml of ethanol and 20 ml of propylene glycol. The therapeutic solution thus prepared is stored in brown dropper bottles.

EXAMPLE 12

Glycolic acid ethanolamine salt 5 percent cream is prepared as follows.

Part A:

Polyoxyethylene (40) stearate: 2 gm
Polyoxyethylene (20) sorbitan monooleate: 1 gm
Glycerol monosterate: 3 gm
Cetyl alcohol: 3 gm
Beeswax: 2 gm
Isopropyl myristate: 1 gm Part B:

Water: 70 ml
Propylene glycol: 3 ml
1,3-Butanediol: 3 ml
Carbomer 940: 0.2 gm

Heat Part A to 75° C. and heat Part B to 80° C. Add Part B slowly to Part A with agitation. Glycolic acid 5 gm and ethanolamine 3 ml are added to the mixture. Continue agitation until the mixture is congealed. Squalene 1 gm, tocopherylacetae 1 gm and retinol palmitate 1 gm are added to the cream with agitation.

EXAMPLE 13

Lactic acid 20 percent gel is prepared as follows.

DL-Lactic acid, USP 20 ml is dissolved in 64 ml of isopropyl alcohol and 14 ml of propylene glycol. Hydroxypropylcellulose, 2 gm is added to the mixture with agitation. Continue agitation until a uniform gel is formed. The therapeutic gel thus prepared may be stored in jars or bottles.

EXAMPLE 14

Lactic acid triethanolamine salt 7% lotion is prepared as follows.

Part A:

Polyoxyethylene (40) stearate: 3 gm
Polyoxyethylene (20) sorbitan monooleate: 2 gm
Glycerol monosterate: 4 gm
Mineral oil: 2 gm
Lanolin: 3 gm Part B:

Water: 60 ml
Propylene glycol: 5 ml
Sorbitol: 3 gm
Glycerol: 3 ml
Carbomer 940: 0.2 gm Heat Part A to 75° C. and heat Part B to 80° C. Add Part B slowly to Part A with agitation. DL-Lactic acid USP 7 ml and triethanolamine 7 ml are added to the mixture. Continue agitation until the mixture is congealed.

EXAMPLE 15

Pyruvic acid 20 percent gel is prepared as follows.

Pyruvic acid 20 ml is dissolved in 68 ml of isopropyl alcohol and 10 ml of propylene glycol. Hydroxypropylcellulose, 2 gm is added to the mixture with agitation. Continue agitation until a uniform gel is formed. The therapeutic gel thus prepared may be stored in jars or bottles.

EXAMPLE 16

Ethyl pyruvate 20 percent solution is prepared as follows.

Ethyl pyruvate 20 ml is dissolved in 64 ml of ethanol and 16 ml of propylene glycol. The therapeutic solution thus prepared is stored in brown dropper bottles.

Test Results

A total of 14 patients having skin keratoses were selected for one study. Each patient was instructed to apply test compositions prepared according to Examples 1 or 3, topically twice daily on the lesions. Standardized color photos were taken of the skin lesions prior to initiating the treatment for comparative reference after 4 to 8 weeks of topical treatment with the test creams or gels. The test results were determined both by clinical evaluation and also by comparison of photos taken before and after treatment. A total of 11 patients showed substantial reduction in the number of keratotic lesions after 4 weeks of topical treatments, with complete resolution of most lesions after 8 weeks of topical treatment. In the remaining 3 patients, partial resolution of keratoses had occurred within the 8 week interval and required more prolonged topical therapy to cause more complete resolution of lesions.

An additional 17 patients having skin keratoses participated in a study of compositions prepared according to Examples 6, 11, 14 or 16. The test results, determined by clinical evaluation as well as by comparison of photos taken before and after treatment, revealed that complete resolution of keratotic lesions occurred in 16 patients after 3 months of topical treatment. In the remaining patient only partial resolution occurred during this interval.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced herein.

What is claimed and desired to be secured by U.S. Letters Patent is:

1. A method for alleviating the symptoms of actinic or nonactinic skin keratoses comprising topically applying to involved areas of the body an effective amount of a composition comprising:
    a therapeutically effective amount of a member selected from the group consisting of α-hydroxybutyric acid, α-hydroxyisobutyric acid, α-hydroxyisocaproic acid, α-hydroxyisovaleric acid, atrolactic acid, β-hydroxybutyric acid, β-phenyl lactic acid, β-phenylpyruvic acid, citric acid, ethyl pyruvate, galacturonic acid, glucoheptonic acid, glucoheptono 1,4-lactone, gluconic acid, gluconolactone, glucuronic acid, glucuronolactone, glycolic acid, isopropyl pyruvate, mandelic acid, methyl pyruvate, mucic acid, pyruvic acid, saccharic acid, saccharic acid 1,4-lactone, tartaric acid and tartronic acid in a pharmaceutically acceptable vehicle.

2. The method of claim 1 wherein said composition further comprises a base selected from the group consisting of ammonium hydroxide, an organic primary, secondary, tertiary or quaternary alkylamine, alkanolamine, diamine, dialkylamine, dialkanolamine, alkylalkanolamine, trialkylamine, trialkanol amine, dialkyl alkanolamine, or alkyl dialkanolamine wherein the alkyl or alkanol substituent has from 1 to 8 carbon atoms present in an amount effective to establish a pH of said composition of between 3.0 and 7.5.

3. The method of claim 1 wherein said member is present in a concentration of from 3-to-30 percent by weight of the total composition.

4. The method of claim 3 wherein said member is present in a concentration of from 5-to-20 percent by weight of the total composition.

5. The method of claim 2 wherein said base comprises a member selected from the group consisting of methylamine, ethylamine, monoethanolamine, monoisopropanolamine, ethylenediamine, 1,2-diaminopropane, dimethylamine, diethylamine, diethanolamine, diisopropanolamine, N-methylethanolamine, N-ethylethanolamine, triethylamine, triethanolamine, N-methyldiethanolamine, tri-isopropylamine and choline.

6. The method of claim 1 wherein the vehicle comprises a mixture of water, ethanol and propylene glycol wherein the concentration of ethanol and propylene glycol does not exceed 70 to 30 percent, respectively, of the total composition.

7. The method of claim 6 wherein the vehicle comprises a mixture of water, ethanol, and propylene glycol present in a volume ratio of 40:40:20, respectively.

8. The method of claim 6 wherein the vehicle further comprises a gelling agent present in a concentration of from 0.1 to 5 percent of the total concentration.

9. The method of claim 8 wherein said gelling agent is a member selected from the group consisting of hydroxyethylcellulose, hydroxypropylcellulose, and hydroxypropylmethylcellulose.

10. The method of claim 8 wherein said member is present in a concentration of from 1 to 3 percent of the total composition.

11. The method of claim 1 wherein said vehicle is a member selected from the group consisting of hydrophilic ointment and petrolatum.

12. The method of claim 6 wherein said vehicle comprises water, ethanol, and propylene glycol present in a volume ratio of 30:60:10, respectively.

13. A method for alleviating the symptoms of actinic or nonactinic skin keratoses comprising topically applying to involved areas of the body an effective amount of a composition comprising: a therapeutically effective amount of a product prepared by reacting, in aqueous or alcoholic aqueous solution, an acid selected from the group consisting of α-hydroxybutyric acid, α-hydroxyisobutyric acid, α-hydroxyisocaproic acid, α-hydroxyisovaleric acid, atrolactic acid, β-hydroxybutyric acid, β-phenyl lactic acid, β-phenylpyruvic acid, citric acid, ethyl pyruvate, galacturonic acid, glucoheptonic acid, glucoheptono 1,4-lactone, gluconic acid, gluconolactone, glucuronic acid, glucuronolactone, glycolic acid, isopropyl pyruvate, lactic acid, mandelic acid, methyl pyruvate, mucic acid, pyruvic acid, saccharic acid, saccharic acid 1,4-lactone, tartaric acid and tartronic acid, or the anhydride thereof, and a base selected from the group consisting of ammonium hydroxide, an organic primary, secondary, tertiary or quaternary alkylamine, alkanolamine, diamine, dialkylamine, dialkanolamine, alkylalkanolamine, trialkylamine, trialkanol amine, Dialkyl alkanol amine, or alkyldialkanolamine wherein the alkyl or alkanol substituent has from 1 to 8 carbon atoms in a pharmaceutically acceptable vehicle.

14. The method of claim 13 wherein said composition has a pH of from 3.0 to 7.5.

15. The method of claim 13 wherein said product is present in a concentration of from 3-to-30 percent by weight of the total composition.

16. The method of claim 13 wherein said product is present in a concentration of from 5-to-20 percent by weight of the total composition.

17. The method of claim 13 wherein the vehicle comprises a mixture of water, ethanol and propylene glycol wherein the concentration of ethanol and propylene glycol does not exceed 70 and 30 percent, respectively, of the total composition.

18. The method of claim 17 wherein the vehicle comprises a mixture of water, ethanol, and propylene glycol present in a volume ratio of 40:40:20, respectively.

19. The method of claim 17 wherein the vehicle further comprises a gelling agent present in a concentration of from 0.1 to 5 percent of the total concentration.

20. The method of claim 19 wherein said gelling agent is a member selected from the group consisting of hydroxyethylcellulose, hydroxypropylcellulose, and hydroxypropylmethylcellulose.

21. The method of claim 19 wherein said member is present in a concentration of from 1 to 3 percent of the total composition.

22. The method of claim 13 wherein said vehicle is a member selected from the group consisting of hydrophilic ointment and petrolatum.

23. The method of claim 17 wherein said vehicle comprises water, ethanol, and propylene glycol present in a volume ratio of 30:60:10, respectively.

24. A method for alleviating the symptoms of actinic or non-actinic skin keratoses comprising topically applying to involved areas of the body an effective amount of a composition comprising: a therapeutically effective amount of malic acid in a pharmaceutically acceptable vehicle.

25. The method of claim 24 wherein composition further comprises a base selected from the group consisting of ammonium hydroxide, an organic primary, secondary, tertiary or quaternary alkylamine, alkanolamine, diamine, dialkylamine, dialkanolamine, alkylalkanolamine, trialkylamine, trialkanol amine, dialkyl alkanol amine, or alkyldialkanolamine wherein the alkyl or alkanol substituent has from 1 to 8 carbon atoms in a pharmaceutically acceptable vehicle.

* * * * *